US012807548B2

(12) United States Patent
Tallman et al.

(10) Patent No.: US 12,807,548 B2
(45) **Date of Patent: *Nov. 24, 2026**

(54) PROCESSES FOR CATALYTIC PARAFFIN DEHYDROGENATION AND CATALYST RECOVERY

(71) Applicant: Kellogg Brown & Root LLC, Houston, TX (US)

(72) Inventors: Michael J. Tallman, Houston, TX (US); Manoj Nagvekar, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,501

(22) Filed: Apr. 25, 2022

(65) Prior Publication Data

US 2022/0250049 A1 Aug. 11, 2022

Related U.S. Application Data

(63) Continuation-in-part of application No. 16/823,733, filed on Mar. 19, 2020, now abandoned.
(Continued)

(51) Int. Cl.
*C07C 5/333* (2006.01)
*B01J 8/00* (2006.01)
(Continued)

(52) U.S. Cl.
CPC ............ *C07C 5/3332* (2013.01); *B01J 8/006* (2013.01); *B01J 38/48* (2013.01); *B01J 38/72* (2013.01); *C07C 5/321* (2013.01); *C07C 2523/83* (2013.01)

(58) Field of Classification Search
None
See application file for complete search history.

(56) References Cited

U.S. PATENT DOCUMENTS 5,254,788 A 10/1993 Gartside et al.
5,895,829 A * 4/1999 Popel ........................ C07C 5/42
585/662

(Continued)

FOREIGN PATENT DOCUMENTS

JP 200037625 A 2/2000

OTHER PUBLICATIONS

International Searching Authority, Patent Cooperation Treaty, International Search Report and Written Opinion dated Sep. 1, 2023 for International Application No. PCT/US2023/065960 filed Apr. 19, 2023; 9 pages.

(Continued)

*Primary Examiner* — Renee Robinson
*Assistant Examiner* — Alyssa L Cepluch
(74) *Attorney, Agent, or Firm* — Gary Machetta

(57) ABSTRACT

A paraffin having 2-8 carbon atoms may be dehydrogenated by contacting the paraffin with metal oxide catalyst(s) to produce light olefins, such as propylene, under certain reaction conditions in a riser, fluidized bed, or fixed-bed swing reactor. The resulting metal oxide catalyst fines contained in the reactor effluent stream formed by the dehydrogenation reaction may be recovered by contacting the reactor effluent stream with a wash fluid to form a catalyst effluent stream that is subsequently slurried and filtered to capture the catalyst fines for potential reuse.

17 Claims, 1 Drawing Sheet

Related U.S. Application Data

(60) Provisional application No. 62/821,672, filed on Mar. 21, 2019.

(51) Int. Cl.

| | |
|---|---|
| ***B01J 38/48*** | (2006.01) |
| ***B01J 38/72*** | (2006.01) |
| ***C07C 5/32*** | (2006.01) |

(56) References Cited

U.S. PATENT DOCUMENTS 6,576,804 B1 * 6/2003 Heineke .................. B01J 23/26 585/662
7,011,740 B2 * 3/2006 Tallman ................. C10G 11/18 422/142
7,057,081 B2 * 6/2006 Allison .................. C07C 29/06 568/910.5
11,746,070 B2 * 9/2023 Wang ........................ C07C 5/41 585/379
2001/0049461 A1 * 12/2001 Kishimoto .............. C07C 45/33 568/959
2003/0065235 A1 * 4/2003 Allison .................... B01J 23/34 585/656
2010/0236985 A1 * 9/2010 Luo ....................... C07C 5/3337 208/138
2014/0296605 A1 * 10/2014 Laha ...................... C07C 5/322 502/251
2014/0371504 A1 * 12/2014 Stine ........................ C07C 5/48 585/658
2017/0233312 A1 * 8/2017 Hossain .................... C07C 5/42 585/656
2020/0197891 A1 * 6/2020 Pretz ........................ B01J 8/006
2020/0199043 A1 * 6/2020 Thakur .................. B01J 35/633
2020/0299212 A1 9/2020 Tallman et al.
2022/0080390 A1 * 3/2022 Mukherjee ............ C07C 5/3332
2022/0250049 A1 8/2022 Tallman et al.

OTHER PUBLICATIONS

Intellectual Property India, First Examination Report dated Aug. 23, 2023 for India Application No. 202117046437 filed Oct. 12, 2021, 6 pages.
Korean Notice of Preliminary Rejection dated Feb. 18, 2025 for Korean Application No. 10-2021-7033232 filed Oct. 14, 2021, 4 pages.

* cited by examiner

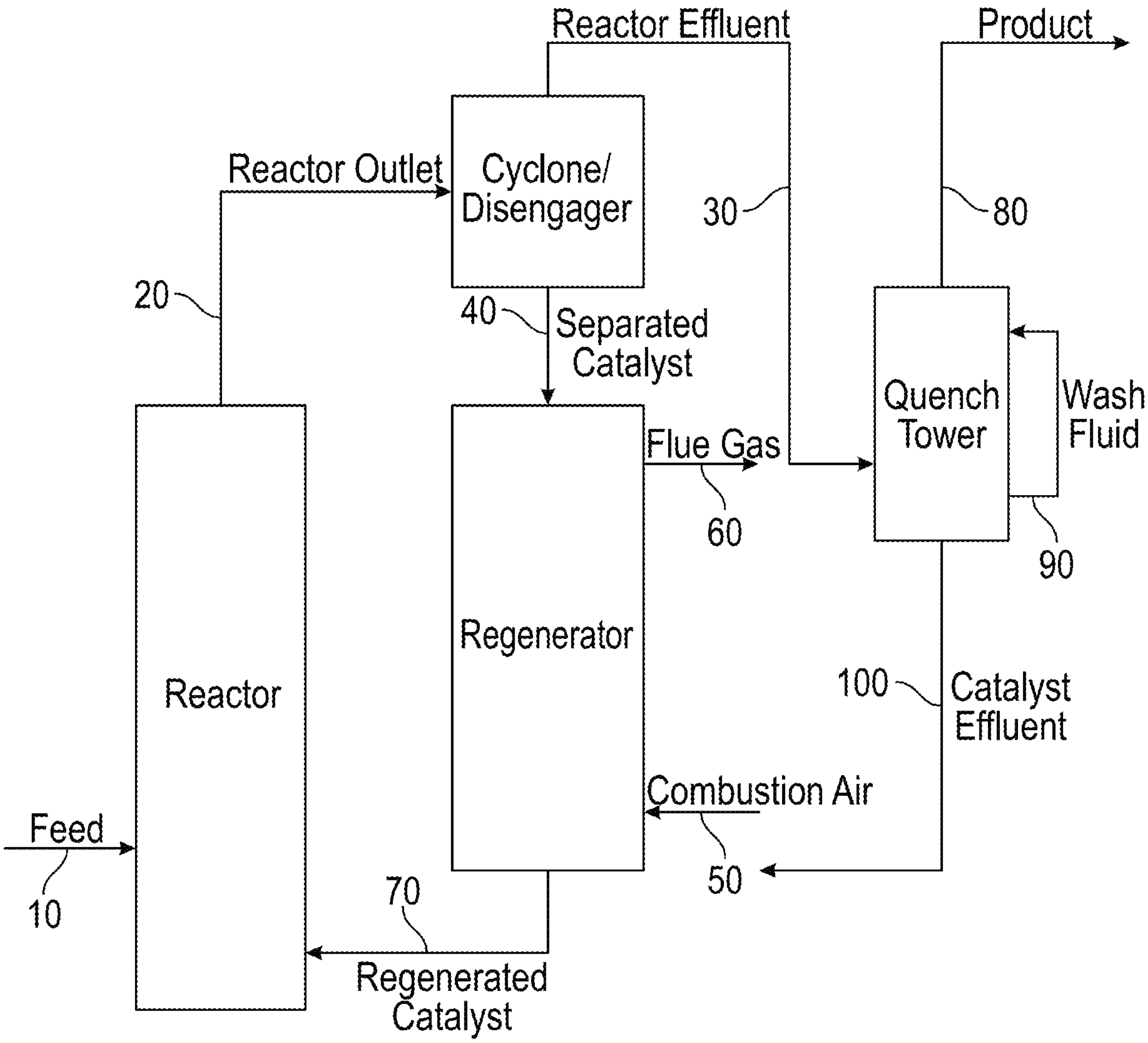
Reactor Effluent
Product
Reactor Outlet
Cyclone/
Disengager
30
80
20
40
Separated
Catalyst
Quench
Tower
Wash
Fluid
Flue Gas
60
90
Regenerator
Reactor
100
Catalyst
Effluent
Combustion Air
Feed
50
10
70
Regenerated
Catalyst

PROCESSES FOR CATALYTIC PARAFFIN DEHYDROGENATION AND CATALYST RECOVERY

CROSS-REFERENCE TO RELATED APPLICATION

This application is a continuation-in-part patent application from U.S. patent application Ser. No. 16/823,733 filed Mar. 19, 2020, incorporated herein in its entirety by reference.

TECHNICAL FIELD

The present invention relates to a process for dehydrogenation of paraffins by reacting a paraffin stream with metal oxide catalyst(s) to produce light olefins, such as propylene, and a process for the recovery of metal oxide catalyst fines from the reactor effluent stream using a wash fluid and filtration.

BACKGROUND

The abundance of alkanes and paraffins from shale and stranded gas has spurned the development of more cost-effective ways to produce light olefins, the demand for which has increased significantly in recent years. Steam cracker units using lighter shale condensates as feedstock have been used to meet the increase in the demand for light olefins, like ethylene. However, these units have been found to be deficient for propylene production due to the low propylene/ethylene ratio and low propylene yield. As a result, finding routes for the targeted production of propylene have received considerable interest.

It has been shown that catalytic dehydrogenation provides the possibility of high selectivity to a single olefin product. Current alkane dehydrogenation processes for the production of propylene and other light olefins employ the use of platinum-based and chromium-based catalysts. Given the expense associated with platinum and the carcinogenic properties of chromium, there is a need for developing less expensive, less toxic metal oxide catalysts that can is capable of good alkene selectivity during the dehydrogenation process and a correspondingly high yield.

A potential deficiency in processes for alkane or paraffin dehydrogenation employing a riser or fluidized-bed type reactor is the amount of catalyst fines in the effluent streams leaving the dehydrogenation reactor. With regard to the reactor effluent stream, a water quench tower is used to cool the reactor effluent and condense the water therein, particularly if dilution steam is used to lower the partial pressure of the alkane or paraffin. The catalyst fines contained in the reactor effluent stream cannot easily be separated from quench water, leading to excessive fouling in the equipment and consequential high maintenance costs. Thus, there is also a need for improved recovery of catalyst fines found in the effluent stream from the dehydrogenation reactor.

BRIEF DESCRIPTION OF THE DRAWINGS

The FIGURE a schematic illustration of a process for catalytic paraffin dehydrogenation and catalyst recovery of the kind described herein.

SUMMARY

There is provided, in one form, a process for dehydrogenating paraffins by contacting a metal oxide catalyst with a paraffin having 2-8 carbon atoms in a riser, fluidized bed, or fixed-bed swing reactor for a reaction period ranging from about 0.05 seconds to about 10 minutes. In one embodiment, the metal oxide catalyst includes an active catalyst including, but not necessarily limited to, zinc, copper, iron, manganese, niobium, and combinations thereof; a catalyst support including, but not necessarily limited to, titanium, aluminum, silicon, and combinations thereof; and a catalyst stabilizer including, but not necessarily limited to, zirconium, cerium, dysprosium, erbium, europium, gadolinium, lanthanum, neodymium, praseodymium, samarium, terbium, ytterbium, yttrium, niobium, tungsten, and combinations thereof, wherein the metal oxide catalyst is substantially free of platinum and chromium.

There is further provided in another form, a process for recovering catalyst fines from the reactor effluent stream of a catalytic paraffin dehydrogenation reaction in a riser or fluidized-bed type reactor, the process comprising: contacting a metal oxide catalyst with a paraffin having 2-8 carbon atoms; generating a reactor effluent stream comprising metal oxide catalyst fines after contacting the metal oxide catalyst with the paraffin; and contacting the reactor effluent stream with a wash fluid to transfer the metal oxide catalyst fines from the reactor effluent stream into the wash fluid and form a cooled catalyst effluent stream and a substantially catalyst-free product stream.

DETAILED DESCRIPTION

It has been discovered that contacting one or more metal oxide catalysts with a paraffin having 2-8 carbon atoms in a dehydrogenation reaction for a period ranging from about 0.05 seconds to about 10 minutes in a reactor may lead to better selectively for the production of certain olefins, such as propylene and ethylene. It has also been discovered that metal oxide catalyst fines, generated because of attrition in a riser or fluidized-bed type reactor, are contained within the reactor effluent stream. These catalyst fines may be recovered by contacting the effluent stream of the reactor with a wash fluid, typically oil or water, to form a cooled catalyst effluent stream and a substantially catalyst-free product stream and then filtering the cooled catalyst effluent stream with a set of filters to capture the catalyst fines for potential reuse.

In one embodiment, the paraffin to be contacted with the metal oxide catalyst(s) may be propane, ethane, n-butane, isobutane, and combinations thereof. In another embodiment, the paraffin may be introduced to the reactor with or without an inert diluent or steam.

The metal oxide catalysts useful in dehydrogenating the paraffin to produce a light olefin product gas may be made up of one or more of the following oxides: zinc, titanium, copper, iron, manganese, aluminum, silicon, zirconium, cerium, dysprosium, erbium, europium, gadolinium, lanthanum, neodymium, praseodymium, samarium, terbium, ytterbium, yttrium, tungsten, or niobium. In a non-limiting embodiment, the metal oxide catalyst(s) used are substantially free of platinum and chromium. In a non-limiting embodiment, the metal oxide catalyst has three sub-groups: active catalyst, support, and stabilizer. In one non-limiting embodiment, the active catalyst includes, but is not necessarily limited to, zinc, copper, iron, manganese, niobium, and combinations thereof. In another non-restrictive version, the catalyst support includes, but is not necessarily limited to, titanium, aluminum, silicon, and combinations thereof. In a different non-limiting embodiment, the catalyst stabilizer includes, but is not necessarily limited to, zirconium, cerium, dysprosium, erbium, europium, gadolinium, lanthanum, neodymium, praseodymium, samarium, terbium, ytterbium, yttrium, niobium, tungsten, and combinations thereof. In particular, zirconium is not an active catalyst component, but is only a stabilizer for the metal oxide catalyst.

The dehydrogenation of the paraffin using metal oxide catalysts of the kinds described above and recovery of catalyst fines in the reactor effluent stream may be accomplished, in one non-limiting embodiment, by the process depicted in the FIGURE in which a paraffin feedstock 10 comprising paraffins having 2-8 carbons is contacted with one or more metal oxide catalysts in a riser or fluidized bed reactor under dehydrogenation conditions. This process may be performed at a reaction temperature of 500-800 °C, a space velocity of 0.1-1 $h^{-1}$, and a pressure of 0.01-0.2 MPa. In one embodiment, the reaction period may range from about 0.05 seconds to about 10 minutes. In other non-limiting embodiments, the dehydrogenation reaction between the paraffin and the metal oxide catalyst(s) may also be carried out in a fixed-bed swing or riser or fluidized-bed reactor from which a reactor outlet stream 20 is formed. The reactor outlet stream 20, in one non-restrictive embodiment, is then sent to a cyclone or disengager to separate catalyst from the reactor outlet stream and form an overhead reactor effluent stream 30.

In a non-limiting embodiment, the reactor effluent stream 30 contains light olefins, such as, without limitation, propylene and/or ethylene. The bulk of the catalyst is retained within the reactor or recovered in the cyclone/disengager and then sent as a separated catalyst stream 40 to a regenerator, which uses combustion air 50 to produce a flue gas stream 60 and a regenerated catalyst stream 70 that is returned to the reactor.

However, some catalyst fines, formed due to attrition in reactor types like riser or fluidized-bed reactors, may be contained in the reactor effluent stream 30. These metal oxide catalyst fines may be recovered in a process in which the reactor effluent stream 30 is contacted in a quench tower with a wash fluid 90, typically oil or water, to transfer the metal oxide catalyst fines from the reactor outlet stream into the wash fluid and form a cooled catalyst effluent stream 100 and a substantially catalyst-free product stream 80. In one non-restrictive embodiment, the reactor effluent stream 30 is contacted with the wash fluid in a quench tower that contains vapor-liquid contacting elements, such as, without limitation, packing or trays. The quench tower, in another embodiment, may also have a recirculation loop for continuously recirculating a wash fluid to the contacting elements.

In another non-restrictive embodiment, the cooled catalyst effluent stream 100 may subsequently be converted into a slurry and then directed to one or more filters to separate the metal oxide catalyst fines. In one embodiment, the slurry is continuously passed through a first filter in a filtration mode to separate the metal oxide catalyst fines therefrom while a second filter in parallel with the first filter is in backflushing mode to remove the separated metal oxide catalyst fines therefrom. The filtration of the slurry may comprise periodically alternating the first and the second filters between filtration and backflushing mode. After filtration, the separated metal oxide catalyst fines may be collected and accumulated in a catalyst accumulator. The catalyst fines may then be prepared for reuse in the dehydrogenation reaction.

In the foregoing specification, the invention has been described with reference to specific embodiments thereof. However, the specification is to be regarded in an illustrative rather than a restrictive sense. For example, paraffins, metal oxide catalysts, dehydrogenation reaction conditions and equipment, and catalyst fine recovery conditions and equipment falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, the process may comprise, consist of, or consist essentially of: contacting a metal oxide catalyst with a paraffin having 2-8 carbon atoms in a reactor for a reaction period ranging from about 0.05 seconds to about 10 minutes.

Alternatively, the recovery of the catalyst fines from a reactor effluent stream may comprise, consist of, or consist essentially of: contacting a metal oxide catalyst with a paraffin having 2-8 carbon atoms, generating a reactor effluent stream comprising metal oxide catalyst fines after contacting the metal oxide catalyst with the paraffin, and contacting the reactor effluent stream with a wash fluid to transfer the metal oxide catalyst fines from the reactor effluent stream into the wash fluid and form a cooled catalyst effluent stream and a substantially catalyst-free product stream.

The present invention may suitably comprise, consist of, or consist essentially of the elements disclosed and may be practiced in the absence of an element not disclosed. For instance, there is provided a process for dehydrogenating paraffins, the process comprising, consisting essentially of, or consisting of, contacting a metal oxide catalyst with a paraffin having 2-8 carbon atoms for a reaction period ranging from about 0.05 seconds to about 10 minutes in a reactor for a catalytic paraffin dehydrogenation reaction wherein: the metal oxide catalyst comprises, consists essentially of, or consists of an active catalyst selected from the group consisting of zinc, copper, manganese, niobium, and combinations thereof; a catalyst support selected from the group consisting of titanium, aluminum, silicon, and combinations thereof; and a catalyst stabilizer selected from the group consisting of zirconium, cerium, dysprosium, erbium, europium, gadolinium, lanthanum, neodymium, praseodymium, samarium, terbium, ytterbium, yttrium, niobium, and combinations thereof; and the metal oxide catalyst is free of platinum and chromium.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

Kellogg Brown & Root LLC and Exelus Inc. were parties to a joint research and development agreement.

What is claimed is:

1. A process for recovering catalyst fines from a reactor effluent stream of a catalytic paraffin dehydrogenation reaction, the process comprising:

a. contacting a metal oxide catalyst with a paraffin having 2-8 carbon atoms for a reaction period ranging from about 0.05 seconds to about 10 minutes in a reactor to dehydrogenate the paraffin wherein:

the metal oxide catalyst consists of:

an active catalyst selected from the group consisting of oxides of zinc, copper, niobium, and combinations thereof;

a catalyst support selected from the group consisting of oxides aluminum and silicon; and a catalyst stabilizer selected from the group consisting of oxides of zirconium, cerium, dysprosium, erbium, europium, gadolinium, lanthanum, neodymium, praseodymium, samarium, terbium, ytterbium, yttrium, niobium, and tungsten; and b. generating a reactor effluent stream comprising metal oxide catalyst fines after the contacting; and c. washing the reactor effluent stream with a wash fluid to transfer the metal oxide catalyst fines from the reactor effluent stream into the wash fluid and form a cooled catalyst effluent stream comprising the metal oxide catalyst fines and a catalyst-free product stream.

2. The process of claim 1, wherein the reactor is a riser reactor, fluidized bed reactor, or a fixed-bed swing reactor.

3. The process of claim 1, wherein the paraffin is selected from the group consisting of propane, ethane, n-butane, isobutane, and combinations thereof.

4. The process of claim 1, wherein the reactor effluent comprises an olefin selected from the group consisting of propylene, ethylene, and combinations thereof.

5. The process of claim 1, wherein the contacting occurs at a temperature ranging from about 500 °C to about 800 °C.

6. The process of claim 1, wherein the contacting occurs at a pressure ranging from about 0.01 MPa to about 0.02 MPa.

7. The process of claim 1, wherein the paraffin is introduced to the reactor with an inert diluent or steam.

8. A process for recovering catalyst fines from a reactor effluent stream of a catalytic paraffin dehydrogenation reaction, the process comprising:

a. contacting a metal oxide catalyst with a paraffin having 2-8 carbon atoms in a reactor;

i. wherein the paraffin is selected from the group consisting of propane, n-butane, isobutane, and combinations thereof;

ii. wherein the metal oxide catalyst consists of:

an active catalyst selected from the group consisting of zinc, copper, niobium, and combinations thereof;

a catalyst support selected from the group consisting of oxides of aluminum, silicon, and combinations thereof; and a catalyst stabilizer selected from the group consisting of oxides of zirconium, cerium, dysprosium, erbium, europium, gadolinium, lanthanum, neodymium, praseodymium, samarium, terbium, ytterbium, yttrium, niobium, tungsten, and combinations thereof;

b. generating a reactor effluent stream comprising metal oxide catalyst fines after the contacting; and c. washing the reactor effluent stream with a wash fluid to transfer the metal oxide catalyst fines from the reactor effluent stream into the wash fluid and form a cooled catalyst effluent stream comprising the metal oxide catalyst fines and a catalyst-free product stream.

9. The process of claim 8, further comprising converting the cooled catalyst effluent stream into a slurry.

10. The process of claim 9, further comprising filtering the slurry in one or more filters to yield separated metal oxide catalyst fines.

11. The process of claim 10, wherein the slurry is continuously passed through a first filter in a filtration mode to separate the metal oxide catalyst fines from the slurry while a second filter in parallel with the first filter is in backflushing mode to remove the separated metal oxide catalyst fines from the second filter.

12. The process of claim 11, wherein the filtration of the slurry comprises periodically alternating the first and the second filters between filtration and backflushing modes.

13. The process of claim 11, wherein the separated metal oxide catalyst fines are accumulated in a catalyst accumulator.

14. The process of claim 8, wherein the reactor effluent stream is washed in a quench tower.

15. The process of claim 14, wherein the quench tower has vapor-liquid contacting elements.

16. The process of claim 14, wherein the quench tower has a recirculation loop for continuously recirculating the wash fluid to the contacting elements.

17. The process of claim 14, wherein the wash fluid comprises oil or water.

* * * * *